(12) United States Patent
Choinski

(10) Patent No.: US 8,961,575 B2
(45) Date of Patent: *Feb. 24, 2015

(54) CMC REPAIR USING SUTURE-BUTTON CONSTRUCT

(75) Inventor: Ronald J. Choinski, Ft. Myers Beach, FL (US)

(73) Assignee: Arthrex, Inc., Naples, FL (US)

( * ) Notice: Subject to any disclaimer, the term of this patent is extended or adjusted under 35 U.S.C. 154(b) by 430 days.

This patent is subject to a terminal disclaimer.

(21) Appl. No.: 13/419,594

(22) Filed: Mar. 14, 2012

(65) Prior Publication Data

US 2013/0245700 A1  Sep. 19, 2013

(51) Int. Cl.
*A61B 17/04* (2006.01)
*A61B 17/80* (2006.01)

(52) U.S. Cl.
USPC ............................ 606/300; 606/232; 606/280

(58) Field of Classification Search
USPC .................. 606/148, 232, 233, 280, 281, 300
See application file for complete search history.

(56) References Cited

U.S. PATENT DOCUMENTS

| | | | |
|---|---|---|---|
| 4,159,716 A | 7/1979 | Borchers | |
| 4,409,974 A | 10/1983 | Freedland | |
| 5,306,301 A | 4/1994 | Graf et al. | |
| 5,529,075 A | 6/1996 | Clark | |
| 5,888,203 A | 3/1999 | Goldberg | |
| 6,391,031 B1 | 5/2002 | Toomey | |
| 6,719,801 B1 | 4/2004 | Holt | |
| 6,964,645 B1 | 11/2005 | Smits | |
| 7,235,091 B2 | 6/2007 | Thornes | |
| 7,875,058 B2 | 1/2011 | Holmes, Jr. | |
| 8,734,491 B2 * | 5/2014 | Seavey | .......................... 606/280 |
| 2003/0023268 A1 | 1/2003 | Lizardi | |
| 2003/0236555 A1 | 12/2003 | Thornes | |
| 2006/0178702 A1 | 8/2006 | Pierce et al. | |
| 2006/0264961 A1 | 11/2006 | Murray-Brown | |
| 2007/0010818 A1 | 1/2007 | Stone et al. | |
| 2008/0177302 A1 | 7/2008 | Shurnas | |
| 2008/0269743 A1 | 10/2008 | McNamara et al. | |
| 2008/0281355 A1 | 11/2008 | Mayer et al. | |
| 2009/0036893 A1 | 2/2009 | Kartalian et al. | |
| 2010/0076504 A1 | 3/2010 | McNamara et al. | |
| 2010/0106254 A1 * | 4/2010 | DelSignore | ................ 623/21.15 |
| 2010/0152752 A1 | 6/2010 | Denove et al. | |
| 2010/0211071 A1 | 8/2010 | Lettmann et al. | |
| 2010/0268273 A1 | 10/2010 | Albertorio et al. | |
| 2011/0118780 A1 | 5/2011 | Holmes, Jr. | |
| 2011/0224729 A1 | 9/2011 | Baker et al. | |

FOREIGN PATENT DOCUMENTS

WO    WO 2009/018527 A1    2/2009

* cited by examiner

*Primary Examiner* — Nicholas Woodall
(74) *Attorney, Agent, or Firm* — Dickstein Shapiro LLP

(57) ABSTRACT

A button and attached suture loop for CMC repair. A suture strand is threaded through holes in the button to attach the button to the suture. The suture ends are then brought together (by being swaged, spliced or cinched together, for example) to form the suture loop comprising a continuous, uninterrupted suture loop with a single strand of swaged-together ends. The swaged-together ends are attached to a suture passing instrument such as a K-wire (Kirschner wire) that is also used to drill a hole through adjoining metacarpals (for example, the first and second metacarpals). The swaged-together ends of the suture are then passed through the drill holes in the first and second metacarpals, and the ends of the suture are pulled until the button abuts one of the first and second metacarpals. A second button is used to secure the cut suture ends to the other metacarpal.

15 Claims, 5 Drawing Sheets

FIG. 7
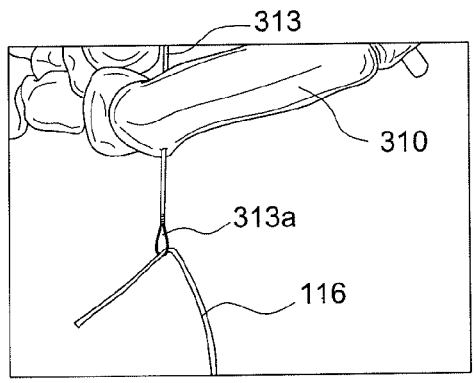
FIG. 8
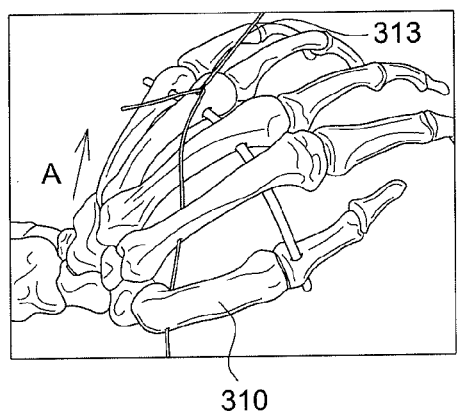
FIG. 9          FIG. 10         FIG. 11
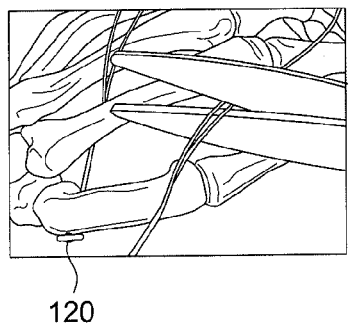 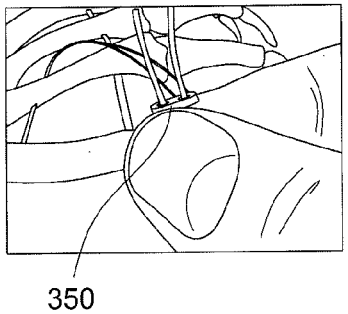 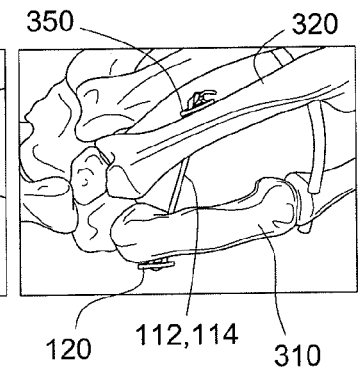

CMC REPAIR USING SUTURE-BUTTON CONSTRUCT

FIELD OF THE INVENTION

The present invention relates to the field of surgery and, in particular, to methods of correcting the space between adjoining bones and treatment of arthrosis and instability, such as CMC (carpometacarpal or Carpal-MetaCarpal) repair or basal joint arthritis, using a suture-button construct and to associated devices.

BACKGROUND OF THE INVENTION

The CMC joint of the thumb is where the metacarpal bone of the thumb attaches to the trapezium bone of the wrist. The CMC joint allows one to move the thumb into the palm, a motion called opposition.

Many types of arthritis can affect this joint, with degenerative basal thumb arthritis being most common. This arthritis may also occur as the result of an injury. The process results in the loss of the protective cartilage cushion of the joint, causing a painful condition where bone rubs on bone. Surgical options for treatment of CMC joint instability and arthritis include trapezium excision, CMC fusion, and Ligament Reconstruction and Tendon Interposition (LRTI), among others.

A new technique with simplified steps and associated system for correcting basal joint arthritis and/or CMC instability are needed. An innovative technique that provides fast patient recovery for one of the most common hand pathologies is also needed.

BRIEF SUMMARY OF THE INVENTION

The present invention provides systems and methods for treatment of joint arthritis or instability in distal extremities. The system (attachment) includes at least one button and a suture loop attached to the at least one button. A suture strand is woven through holes in the button to attach the button to the suture. The suture ends are then brought together (by being swaged, spliced or cinched together, for example) to form the suture loop comprising a continuous, uninterrupted suture loop and a single strand of swaged-together ends attached to the loop. The swaged-together ends are attached to a suture passing instrument such as a K-wire (Kirschner wire) that is also used to drill the hole(s).

A method for correcting the anatomical position of adjoining bones of distal extremities employing the suture-button construct of the present invention (with a continuous suture loop attached to a button) includes inter alia the steps of: (i) providing a swaged suture construct attached to a button by swaging or cinching together ends of a suture strand woven through holes of the button to form a button/suture loop system; (ii) passing the swaged-together ends of the suture through drill holes in the first and second bones (such as two metacarpals); (iii) pulling the ends of the suture until the button abuts one of the bones; (iv) removing (by cutting, for example) the swaged together portion of the suture; (v) attaching the suture ends to another (second) button; (vi) optionally, adjusting the space between the two bones; and (vii) securing the bones in place by the suture-button construct and the second button.

BRIEF DESCRIPTION OF THE DRAWINGS

FIGS. 4-13 illustrate subsequent steps of a method of a CMC repair according to an embodiment of the present invention and employing the swaged suture-button construct of FIG. 2.

DETAILED DESCRIPTION OF THE INVENTION

The present invention provides systems and methods for treatment of joint arthritis or instability in distal extremities. In particular applications, CMC arthritis and/or CMC thumb instability are addressed using a swaged suture-button construct as described in co-owned U.S. Patent Application Publication No. 2011/0224729, the entire disclosure of which is incorporated by reference herein.

The technique allows the formation of drill holes in adjoining bones (such as two adjoining metacarpals), the drill holes having a diameter smaller than the 2.7 mm drill holes formed by known techniques in the art. According to exemplary embodiments, the method of the present invention forms drill holes of reduced diameter of about 1.0 mm to about 2.0 mm, preferably of about 1.1 mm (in lieu of the 2.7 mm drill holes formed by known techniques in the art) in two adjoining metacarpals (for example, first and second metacarpals). The technique simplifies the known techniques in the art by providing only one step (passing a K-wire which also forms/drills the holes in the two metacarpals) and reducing the number of steps (i.e., eliminating the use of guidewires and/or cannulated drill bits).

Figure 1:
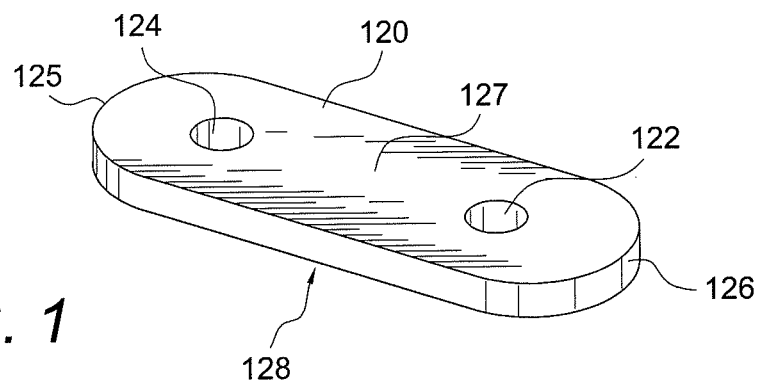
FIG. 1 illustrates a perspective view of an oblong button that forms part of the swaged suture-button construct of the present invention.
Figure 2:
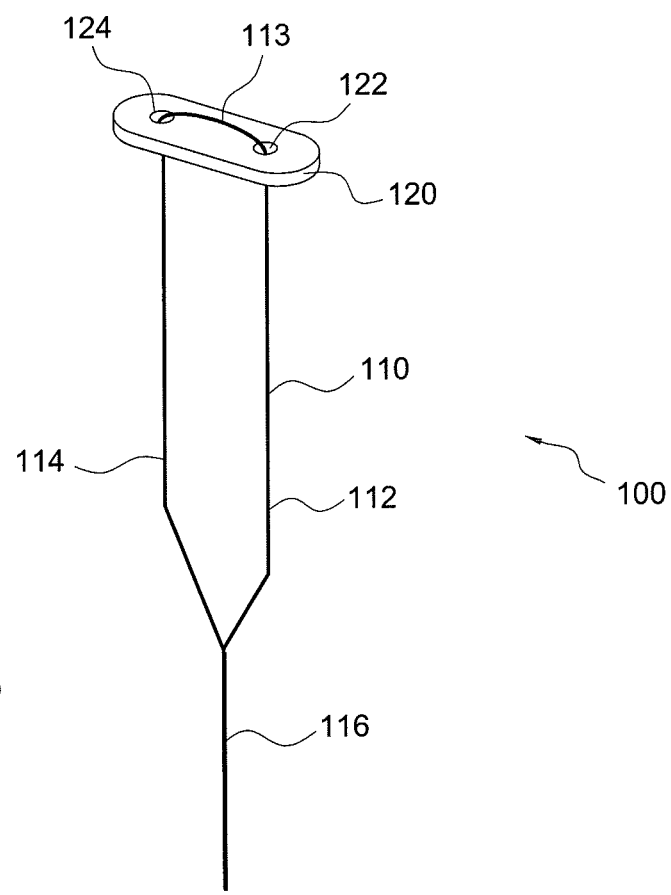
FIG. 2 illustrates an embodiment of a swaged suture-button construct of the present invention.

Referring now to the drawings where like elements are designated by like reference numerals, FIGS. 1 and 2 illustrate swaged suture-button construct 100 of the present invention used, for example, in corrective surgery for treatment of CMC arthritis, thumb CMC instability and revisions with proximal migration after failed tendon reconstruction.

In an exemplary embodiment only, the swaged suture-button construct 100 of the present invention is employed in metacarpal repairs and instabilities, for example, in stabilizing the thumb metacarpal (first metacarpal) following removal or partial resection of the trapezium, and/or for treatment of carpometacarpal arthrosis and instability (for example, between two metacarpals such as the first and second metacarpals).

In the embodiments described below, the swaged suture-button construct 100 provides a unique means to suspend the thumb metacarpal. In certain applications, trapezial resection or removal may be conducted prior to the application of the swaged suture-button construct 100 to the repair. The swaged suture-button construct 100 uses a pulley principle to help reduce the thumb and index metacarpals into proper relationship that is maintained through healing.

FIG. 1 illustrates button 120 used in corrective surgery and as part of swaged suture-button construct 100. Button 120 is an oblong shaped plate with chamfered or rounded corners and edges. Button 120 has a length that extends from proximal end 125 to distal end 126. Button 120 further has a width that is shorter than the length. Button 120 also has front face 127 and back face 128, wherein the distance between the front and back face 127, 128 is smaller than the width of button 120. In another embodiment, the distance between front and back face 127, 128 is greater than the width of button 120.

Button 120 further includes holes 122 and 124 that extend from front face 127 to back face 128. Hole 122 is located near distal end 126. Hole 124 is located near proximal end 125. Holes 122 and 124 are of sufficient diameter to allow suture 110 to pass through, but not so large as to severally compromise the integrity and strength of button 120.

FIG. 2 illustrates an exemplary embodiment of suture-button construct 100 (attachment 100) that includes a suture 110 and a button 120. Suture 110 is a threadlike material that is commonly employed in surgery to hold tissue or bone together. In this embodiment, suture 110 is a FiberWire® suture from Arthrex, described in U.S. Pat. No. 6,716,234. In other embodiments, different types of sutures and different sizes of sutures may be used.

As shown in FIG. 2, suture 110 passes through first hole 122 of button 120 and through second hole 124. As a result, suture 110 includes first leg 112 that passes through hole 122 and extends away from back face 128 and second leg 114 that passes through hole 124 and also extends away from back face 128. Suture 110 also includes connecting leg 113 that extends between first hole 122 and second hole 124 along front face 127 of button 120.

In suture-button construct 100, first leg 112 and second leg 114 of suture 110 are swaged together to form combined leg 116 (single tail 116) of suture 110. As a result, part of suture 110 is formed into a continuous, uninterrupted loop with the loop portion of suture 110 passing through holes 122 and 124 of button 120.

As detailed below, single tail 116 (combined leg 116) has a diameter which is about equal to, or smaller than, the diameter of the holes formed through the two metacarpals (for example, the first and second metacarpals) to allow easy passage of the single tail and attached loop through the holes. Preferably, single tail 116 (combined leg 116) has a diameter smaller than about 2.7 mm, for example, of about 1.0 mm to about 2.0 mm. Preferably, single tail 116 has a diameter of about 1.1 mm. The diameter of single tail 116 is preferably constant throughout the length of the tail 116.

Figure 3A:
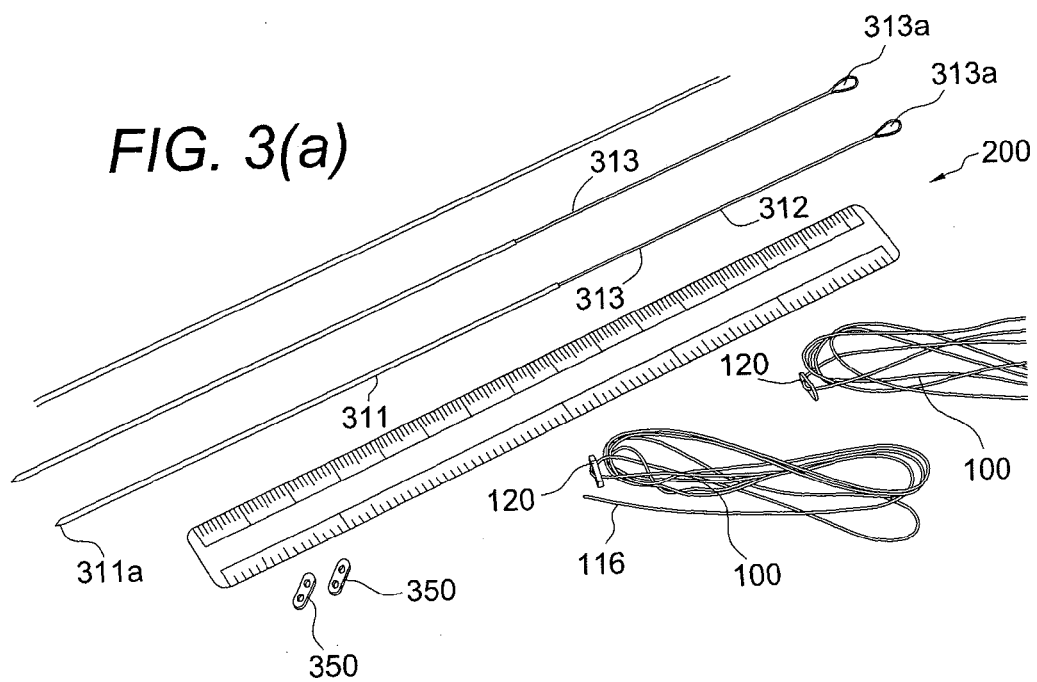
FIG. 3(a) illustrates an embodiment of a kit comprising two swaged suture-button constructs, two additional second buttons and a step-off K-wire.
Figure 3B:
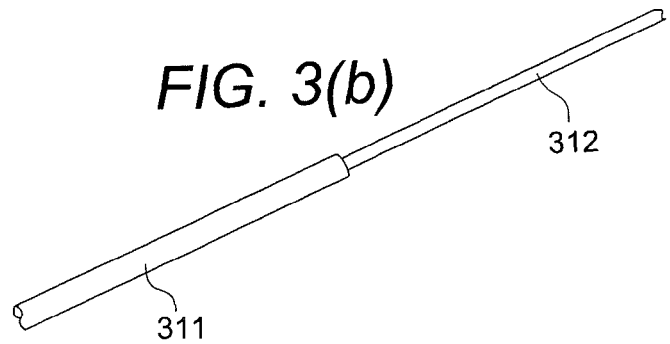
FIG. 3(b) illustrates a detailed, enlarged view of the step-off region of the K-wire of FIG. 3(a).

FIG. 3(a) illustrates an exemplary kit 200 comprising two swaged suture-button constructs 100, two additional fixation devices (for example, two additional second buttons 350 such as round and/or oblong buttons or combination of round and oblong buttons), and a suture passing instrument (K-wire) 313. In an exemplary embodiment, the K-wire 313 has a step-off configuration in that it comprises at least two different regions of different diameters, for example, a first region 311 of a first diameter and a second region 312 of a second diameter, which is different (smaller) than the first diameter (FIG. 3(b)). The first diameter is about 1.0 to about 2.0 mm, preferably of about 1.1 mm (to allow drilling a corresponding hole of about 1.0 to about 2.0 mm, preferably of about 1.1 mm). In yet other exemplary embodiments, the K-wire may be a tapered K-wire provided with a tapered configuration, i.e., with a diameter tapering (decreasing) from most distal end (where the diameter is about 1.0 to about 2.0 mm, preferably of about 1.1 mm) to a proximal end.

Figure 3C:
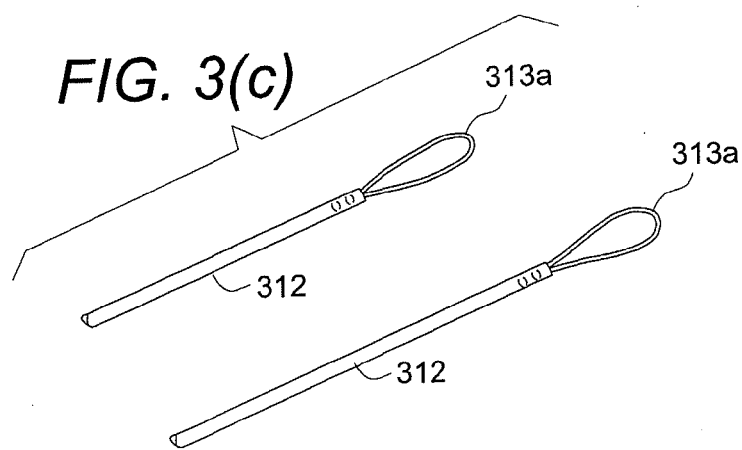
FIG. 3(c) illustrates detailed, enlarged views of the loop of the K-wire of FIG. 3(a).

Most distal end of first region 311 is provided with a drive end 311a to allow the K-wire 313 to form first and second holes 310a, 320a through the first and second metacarpals 310, 320, as detailed below. A loop 313a (shown in more detail in FIG. 3(c)) is provided at a most proximal end of the K-wire 313. Loop 313a is preferably a nitinol loop. As detailed below, the suture passing K-wire is used to both drill holes through the metacarpals and to also shuttle the swaged two-strands suture-button construct (two-stranded Mini TightRope®) through the metacarpals.

Figure 14:
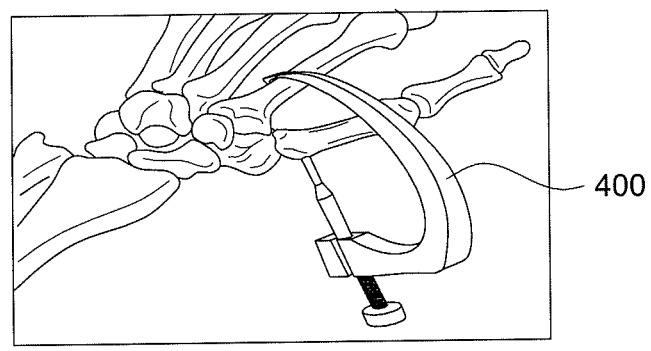
FIG. 14 illustrates a schematic view of a patient's hand undergoing a CMC repair with a C-ring guide and according to the present invention.

Kit 200 may be a sterile, single use, disposable kit that may further include an aiming C-ring guide 400 (FIG. 14) in addition to the K-wire(s), button(s) and the swaged suture-button construct(s) 100.

The swaged suture-button construct 100 (attachment 100) may be used as a suspensionplasty in CMC arthritis, and as part of novel and innovative techniques that provide fast patient recovery for common hand pathologies. The swaged 1.1 mm suture-button construct 100 offers advantages over the known 2.7 mm technique in that it allows for the formation of a smaller-diameter drill hole instead of the 2.7 mm hole, and simplifies the technique by eliminating steps. In a specific, exemplary-only embodiment, the drill hole is about 1.1 mm.

Figure 12:
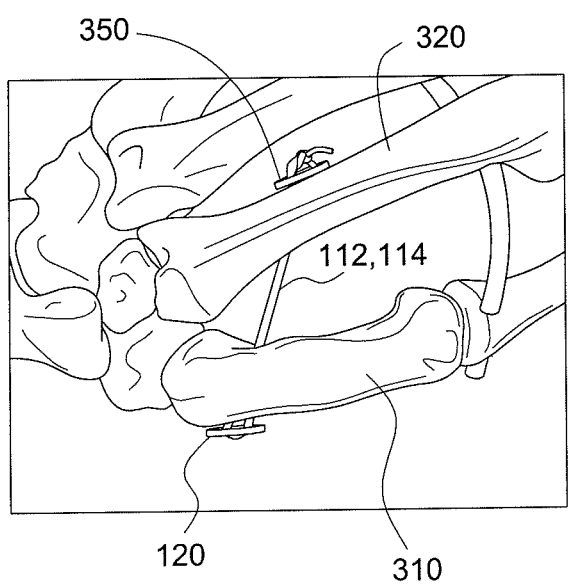
Figure 13:
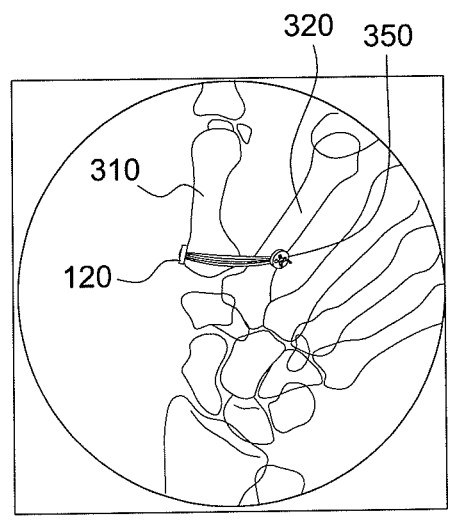

FIGS. 11-13 illustrate exemplary CMC repairs (in the final stage) with the suture-button construct 100 (attachment 100) of the present invention. In an exemplary embodiment, construct 100 is employed to connect two metacarpals, for example, first and second metacarpals 310, 320. A hole 310a, 320a is drilled using a suture passing K-wire 313 through first metacarpal 310 and second metacarpal 320, drilling from first metacarpal 310 to the second metacarpal 320. Suture-button construct 100 is loaded on the K-wire with combined leg 116 of suture 110 attached to the K-wire. Combined leg 116 of suture 110 is shuttled completely through the holes in first metacarpal 310 and second metacarpal 320 by the K-wire. Suture 110 then continues to be shuttled through until button 120 of attachment 100 rests against the lateral cortex of first metacarpal 310.

Combined leg 116 of suture-button construct 100 has a diameter which is about equal to, or smaller than, the diameter of the hole 310a, 320a formed through the two metacarpals 310, 320. Preferably, combined leg 116 and hole 310a, 320a have a diameter of about 1.0 to about 2.0 mm, preferably of about 1.1 mm.

With button 120 resting against first metacarpal 310, first leg 112 and second leg 114 of suture 110 will have been shuttled through the holes in first metatarsal 310 and second metatarsal 320. First and second legs 112, 114 of suture 110 are then cut from combined leg 116, leaving first and second legs 112, 114 protruding from the hole in second metacarpal 320.

A fixation device (for example, a second button 350 such as a round or oblong button 350) is then placed over first and second legs 112, 114 protruding from the hole in second metacarpal 320. First and second legs 112, 114 of suture 110 should be of sufficient length to extend through both the first and second metacarpals 310, 320 and allow for the surgeon to comfortably tie first and second legs 112, 114 over the top of second button 350.

The surgeon then may optionally adjust the metacarpal interspace between the two metacarpals 310, 320. Suture-button construct 100 in combination with second button 350 secure first metacarpal 310 at a proper intermetacarpal angle.

FIGS. 4-10 illustrate in detail the steps of a method of correcting problems associated with adjoining metacarpals employing the 1.1 mm swaged suture-button construct 100 of the present invention. A ligament transfer may be optionally performed in conjunction with the exemplary CMC repair detailed below.

Figure 4:
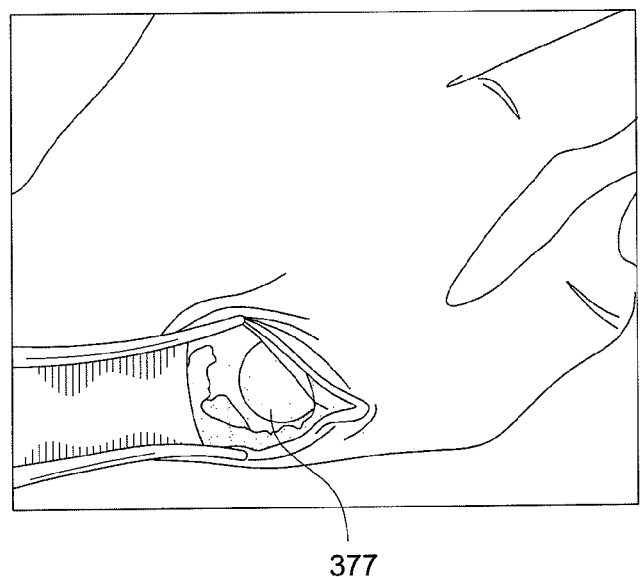

FIG. 4: A 3-4 cm dorsoradial skin incision is created over the trapezium metacarpal joint. The radial artery is safely retracted by means of a vessel loop, taking care to protect the various branches of the radial nerve. A longitudinal incision is made on the capsule and a sharp dissection is made through the abductor/adductor pollicis, which is attached to the radial base of the thumb metacarpal.

Optionally, the trapezium 377 is resected or removed to eliminate the bone-on-bone contact that causes the pain.

A small incision (of about 3-4 mm) is made between the second and third metacarpal bases, to view the ulnar base of the index metacarpal (the eventual exit point of the drill).

Figure 5:
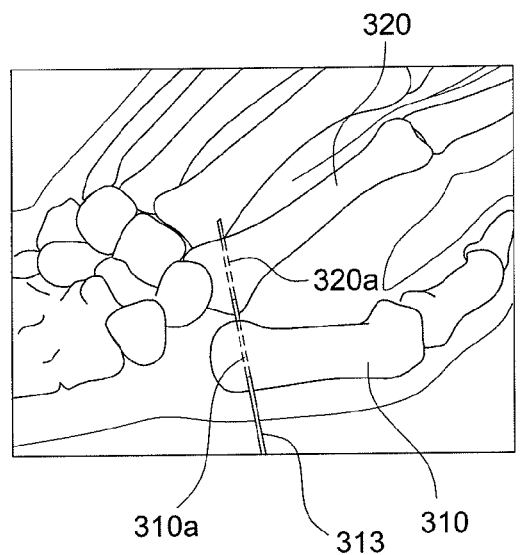
Figure 6:
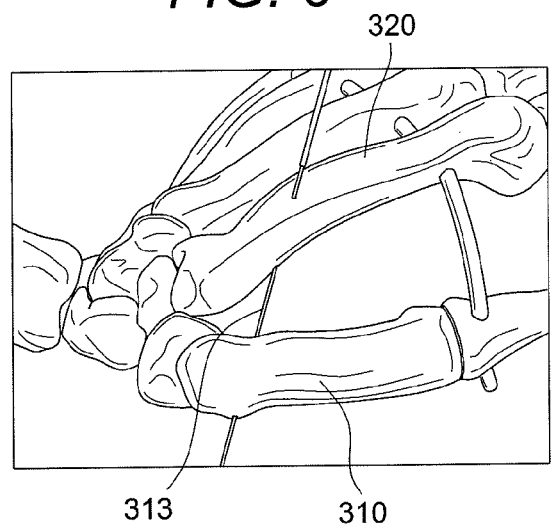

FIGS. 5 and 6: A K-wire 313, preferably a tapered step-off K-wire 313 with a loop 313a (preferably a nitinol loop), is placed from the base of first metacarpal 310 through to the second metacarpal 320. The thumb may be placed in a relaxed neutral position and the tapered K-wire 313 may be started on the dorsal-radial aspect of the first metacarpal base 310. The K-wire 313 may be provided as part of kit 200 together with the construct 100 and additional button(s) 350. The K-wire is preferably a tapered 1.1 mm K-wire.

In repairs which do not require excision or partial resection of the trapezium (as shown in FIG. 6), the K-wire 313 is driven through the second metacarpal 320, aiming for the proximal one third of the second metacarpal shaft. The K-wire should preferably exit in the center of the second metacarpal 320 so that button 120 of the swaged suture-button construct 100 will be buried in the metacarpal interspace. A C-ring guide 400 (FIG. 14) may assist in aiming the K-wire 313 across the metacarpals 310, 320. If employed, the C-ring guide 400 could have a slightly larger cannulation than the 1.1 mm K-wire.

Once the K-wire 313 is in proper position and through both metacarpals 310, 320, the K-wire 313 is driven forward until the thinner tapered portion 312 of the wire is through both bones 310, 320 and slides easily.

FIG. 7: The single swaged suture end 116 of the swaged suture-button construct 100 is fed into the loop 313a of the tapered K-wire 313. Approximately 1 inch of the suture tail 116 may be placed into the loop 313a to ease in suture passage.

FIG. 8: The K-wire 313 and suture construct 100 is pulled through the metacarpals 310, 320 (in the direction of arrow A).

FIG. 9: The swaged suture-button construct 100 is pulled to position button 120 on the lateral cortex of the first metacarpal 310 (radial side). The end of the swaged suture-button construct 100 is cut proximal to the swaged portion 116 to create two tails.

FIG. 10: Another, second button 350 (for example, an oblong button similar to button 120 or a round button) is fed through the free suture tails of the construct 100. Once the slack is removed, at least one knot (for example, 3 to 5 knots) is tied to secure the construct. The trapezial space may be left empty, or filled with an allograft spacer.

Using the 1.1 mm swaged technique of the present invention eliminates the "cinch" effect which may occur with the 2.7 mm technique. Preferably, the drill hole on the base of the thumb is located on the dorsal-radial aspect of the first metacarpal 310 and the K-wire 313 aimed across, while the thumb is in a neutral anatomic position. When a ligament transfer is performed in conjunction with the swaged suture-button construct 100, a bone bridge (preferably of about 5 mm) between the two tunnels may be maintained for support.

Preferably, the procedure is conducted close to the center of the base of the second metacarpal 320 so the button 350 is located in the second-third metacarpal interspace. This will keep the button 350 protected from causing any irritation.

Knots may be tied on the ulnar side (second-third interspace) and the knotless button 120 placed on the radial side (base of thumb).

The key advantages of the CMC suture-button construct technique of the present invention include, among others:
  solid and stable suspensionplasty
  prevention of proximal migration of the first MTC (metacarpal)
  stable but not rigid fixation
  fast technique that saves OR time
  no tendon harvest required
  less morbidity and surgical time
  allows earlier rehabilitation
  suture (FiberWire® suture) has little stretch
  promotes scarring with micromotion
  flexible suture-based fixation The CMC repair may be conducted in an ulnar to radial direction as explained above (ulnar to radial approach where the K-wire with attached swaged suture is pulled from ulnar to radial along the K-wire) or in a radial to ulnar direction (i.e., by conducting steps in a direction opposite to the ulnar to radial direction).

If two or more constructs 100, 100a are employed for the repair, the first of two suture-button constructs 100, 100a is tied down with one knot while the second construct 100, 100a is placed adjacent (for example, proximal to) the first construct. The second construct 100a may be placed in a manner similar to that for the placement of construct 100 (detailed above) with same drilling and passing instructions (i.e., with same suture passing instrument). Swaged suture-button constructs 100, 100a may be used in combination with additional fixation devices (such as second buttons 350, 350a) for securing metacarpals at proper metacarpal interspace. FIG. 13 illustrates an X-ray depiction of the final construct of FIG. 12.

The technique and construct of the present invention provide a significant advantage in that it reduces the size of the drill hole from 2.7 mm to smaller diameter holes (such as 1.0-1.1 mm), preventing bone mass in metacarpals, and simplifies known techniques in the art by providing only one step (i.e., passing the K-wire) as opposed to a three-step process previously employed (i.e., use of a K-wire, drill, and pass the suture-button construct).

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of carpometacarpal repair, comprising the steps of:
  drilling a hole through a first metacarpal and a second metacarpal;
  providing a button/loop construct comprising a button with at least a pair of apertures, and a continuous flexible strand loop connected to the button by passing the flexible strand through the apertures, with opposing ends of the flexible strand terminating in a combined leg;
  passing the combined leg and the loop of the button/loop construct through the hole so that the loop extends through the hole in the first and second metacarpals, and pulling the combined leg and the loop so that the combined leg and part of the loop exit the hole on a lateral side of one of the metacarpals, and the button rests against a lateral cortex of the other metacarpal;
  removing the combined leg so that the opposing ends of the loop are free; and securing the free opposing ends to the lateral side of one of the metacarpals.

2. The method of claim 1, wherein the first metacarpal is the thumb.

3. The method of claim 1, wherein the hole has a diameter smaller than about 2.7 mm.

4. The method of claim 3, wherein the hole has a diameter of about 1.0 mm to about 2.0 mm.

5. The method of claim 4, wherein the hole has a diameter of about 1.1 mm.

6. The method of claim 4, wherein the combined leg has a diameter of about 1.1 mm.

7. The method of claim 1, wherein the combined leg has a first diameter and the hole has a second diameter, the first diameter being about equal to or smaller than the second diameter.

8. The method of claim 1, wherein the step of securing the free opposing ends to the lateral side of one of the metacarpals further comprises the step of attaching the free opposing ends to a fixation device and securing the fixation device to the one of the metacarpals.

9. The method of claim 8, wherein the fixation device is a second button.

10. The method of claim 1, further comprising the steps of drilling the hole through the first and second metacarpals with a suture passing instrument; attaching the combined leg of the button/loop construct to the same suture passing instrument; and passing the combined leg and the loop through the hole.

11. The method of claim 10, wherein the suture passing instrument has a body with a tapered configuration along a longitudinal axis.

12. The method of claim 10, wherein the suture passing instrument is a K-wire with a diameter of about 1.0 mm to about 2.0 mm.

13. The method of claim 12, wherein the diameter of the K-wire is about 1.1 mm.

14. The method of claim 1, further comprising an initial step of removing or partially excising the trapezium.

15. The method of claim 1, wherein the carpometacarpal repair is at least one of carpometacarpal basal joint arthrosis, carpometacarpal arthritis, thumb instability and carpometacarpal fusion.

* * * * *